(12) United States Patent
Wenzel et al.

(10) Patent No.: US 10,578,599 B2
(45) Date of Patent: Mar. 3, 2020

(54) SYSTEM, APPARATUS, AND METHOD FOR MEASURING ION CONCENTRATION WITH A STANDARD DEVIATION CORRECTION

(71) Applicant: SupraSensor Technologies, LLC, Eugene, OR (US)

(72) Inventors: Andreas M. Wenzel, Eugene, OR (US); Jordan Richard Kusiek, Eugene, OR (US); Calden Carroll Stimpson, Eugene, OR (US); Sean Fontenot, Eugene, OR (US)

(73) Assignee: SupraSensor Technologies, LLC, Eugene, OR (US)

( * ) Notice: Subject to any disclaimer, the term of this patent is extended or adjusted under 35 U.S.C. 154(b) by 786 days.

(21) Appl. No.: 15/148,393

(22) Filed: May 6, 2016

(65) Prior Publication Data

US 2016/0327511 A1 Nov. 10, 2016

Related U.S. Application Data

(60) Provisional application No. 62/158,721, filed on May 8, 2015.

(51) Int. Cl.
*G01N 27/416* (2006.01)
*G01N 27/414* (2006.01)
(Continued)

(52) U.S. Cl.
CPC ........... *G01N 33/24* (2013.01); *G01N 27/414* (2013.01); *G01N 33/188* (2013.01); *G01N 2033/245* (2013.01)

(58) Field of Classification Search
CPC ............. G01N 27/333; G01N 27/3335; G01N 27/302; G01N 27/414–4148;
(Continued)

(56) References Cited

U.S. PATENT DOCUMENTS 4,944,274 A 7/1990 Itsuji et al.
5,112,454 A 5/1992 Tanaka et al.
(Continued)

FOREIGN PATENT DOCUMENTS

GB 2 509 127 A 6/2014
WO WO 2009/157755 A2 12/2009

OTHER PUBLICATIONS

Piper et al., "Designing an Autonomous Soil Monitoring Robot" Sieds dated 2015, IEEE, pp. 137-141.
(Continued)

*Primary Examiner* — Gurpreet Kaur
(74) *Attorney, Agent, or Firm* — Hickman Palermo Becker Bingham LLP

(57) ABSTRACT

Embodiments of the inventive concept include a portable ion concentration apparatus including a controller, a storage section to store one or more data samples, an amplifier circuit, and a chemical field effect transistor (CHEMFET). The CHEMFET and the amplifier circuit can indicate a quantity of nitrate levels in a sample media or a reference media. The controller can process the indication of the quantity of nitrate levels, and generate the one or more data samples based at least on the indication of the quantity of nitrate levels. The portable ion concentration apparatus can include an in-field analysis apparatus, an in-field measurement apparatus, or an in-soil monitoring apparatus. A measurement logic section can determine an ion concentration based on a sensitivity slope M or a polynomial fit. Also disclosed is a method for measuring ion concentration with a standard deviation correction.

13 Claims, 10 Drawing Sheets

(51) Int. Cl.
*G01N 33/24* (2006.01)
*G01N 33/18* (2006.01)

(58) Field of Classification Search
CPC ... G01N 27/4165–4168; G01N 27/301; G01N 30/86; G01N 30/8627; G01N 2030/862; H01L 29/2924; H01L 29/13073
See application file for complete search history.

(56) References Cited

U.S. PATENT DOCUMENTS

| | | | | |
|---|---|---|---|---|
| 5,804,971 | A * | 9/1998 | Cumming | G01N 27/286 204/406 |
| 7,927,883 | B2 * | 4/2011 | Tuli | G01V 9/00 422/82.01 |
| 2004/0132204 | A1 * | 7/2004 | Chou | G01N 27/4148 436/163 |
| 2012/0001646 | A1 * | 1/2012 | Bolander | G01R 31/2621 324/679 |
| 2012/0261260 | A1 * | 10/2012 | Li | G01N 27/333 204/416 |
| 2014/0345394 | A1 | 11/2014 | Schildroth | |
| 2015/0076567 | A1 | 3/2015 | Stimpson et al. | |

OTHER PUBLICATIONS

European Search Report in application No. PCT/US2016/031129, dated Sep. 26, 2016, 3 pages.
European Claims in application No. PCT/US2016/031129, dated Sep. 2016, 6 pages.
Wilson et al., "Chemical Sensors for Portable, Handheld Field Instruments", IEEE Sensors Journal, vol. 1, No. 4, dated Dec. 2001, 19 pages.
Reinhoudt et al., "A Novel Architecture for CHEMFETS; the Integration of Sensing Molecules and Membranes", VCH Verlagsgsesellschaft, dated 1992, 18 pages.
Nazarudin et al. "Characterization of Acrylate-based ChemFET Sensor for Nitrate Sensing and Monitoring" dated 2014, IEEE Conference on Biomedical Engineering dated Dec. 2014, 5 pages.
L'Hereec, Frederic, "Solid State Chemical Electronics", School of Electrical and Computer Engineering, Georgia Institute of Technology, Nov. 2003, 74 pages.
Gieling et al., "ISE and Chemfet Sensors in Greenhouse Cultivation", Science Direct, Elsevier B.V., dated 2004, 7 pages.
Diallo et al., "Modelling of Impulsional pH Variations Using ChemFET-Based Microdevices: Application to Hydrogen Peroxide Detection", Sensors 2014, dated Feb. 19, 2014, 17 pages.
The International Bureau of WIPO, "International Preliminary Report on Patentability", in application No. PCT/US2016/031129, dated Nov. 14, 2017, 14.
Current Claims in application No. PCT/US2016/031129, dated Nov. 2017, 6 pages.
Piper et al., "Designing an Autonomous Soil Monitoring Robot", Sieds, dated 2015, IEEE, Systems and Information Engineering Design Smposium, 6 pages.
Martinez-Olmos et al., "Multisensor Probe for Soil Monitoring", Sensors and ActuatorsB: Chemical: International Journal Devoted to Research, vol. 160, No. 1, dated Jul. 5, 2011, 8 pages.
European Patent Office, "Search Report" in application No. PCT/US2016/031129, dated Jan. 10, 2017, 32 pages.
European Claims in application No. PCT/US2016/031129, dated Jan. 2017, 6 pages.

* cited by examiner

SYSTEM, APPARATUS, AND METHOD FOR MEASURING ION CONCENTRATION WITH A STANDARD DEVIATION CORRECTION

BENEFIT CLAIM

This application claims the benefit under 35 U.S.C. § 119 of provisional application 62/158,721, filed May 8, 2015, the entire contents of which are hereby incorporated by reference for all purposes as if fully set forth herein.

FIELD OF THE INVENTION

This application pertains to ion concentration measurement, and more particularly, to an ion concentration measurement system, apparatus, and method for measuring ion concentration with a standard deviation correction in non-laboratory settings.

BACKGROUND

Of the total nitrate fertilizer used in the US, approximately 30% is lost due to over-application and subsequent seepage into groundwater, volatilization or tiling and runoff. New techniques in irrigation and soil moisture monitoring have provided growers improved data to manage irrigation, allowing for better forecasting and immediate feedback resulting in decreased water costs and optimized management practices.

However, conventional devices or systems that measure ion concentration in soil may have ion interference from other ions outside the target ion being measured. The conventional devices or systems may also have drift problems associated to the inherit material of the sensor, or in particular for environmental applications, suffer from deviations in measurement due to turbidity in the sample or other heterogeneous conditions or contaminants. Such interference and drift cause errors during signal processing and lead to the devices or systems reporting inaccurate values.

Accordingly, a need remains for improved devices, systems, and methods for increasing the accuracy of ion concentration measurement in non-laboratory settings. Embodiments of the invention address these and other limitations in the prior art.

Figure 1A:
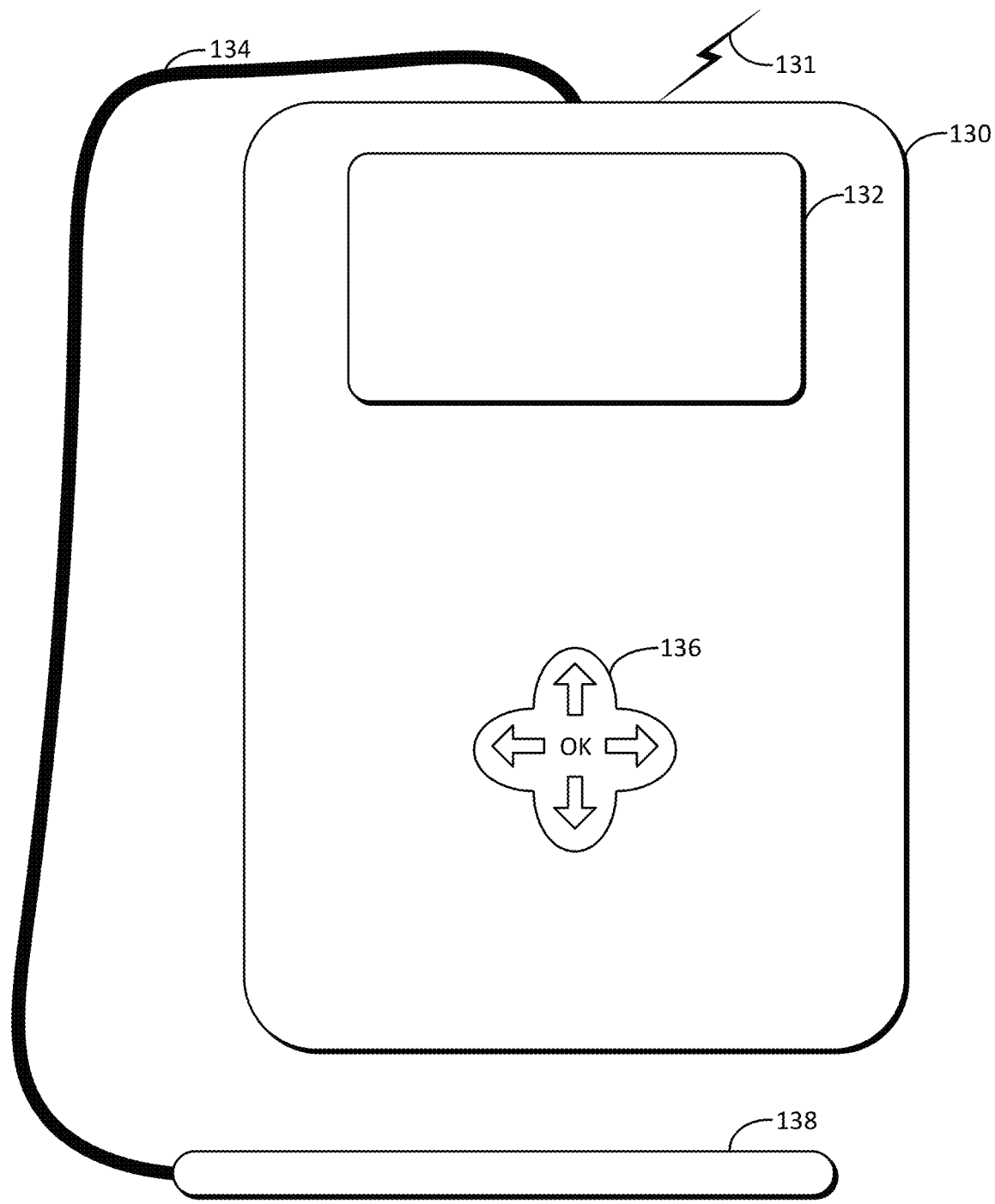
FIG. 1A illustrates an example portable in-field analysis apparatus, in accordance with some embodiments of the present invention.

The foregoing and other features of the invention will become more readily apparent from the following detailed description, which proceeds with reference to the accompanying drawings.

DETAILED DESCRIPTION OF THE EMBODIMENTS

Reference will now be made in detail to embodiments of the inventive concept, examples of which are illustrated in the accompanying drawings. The accompanying drawings are not necessarily drawn to scale. In the following detailed description, numerous specific details are set forth to enable a thorough understanding of the inventive concept. It should be understood, however, that persons having ordinary skill in the art may practice the inventive concept without these specific details. In other instances, well-known methods, procedures, components, circuits, and networks have not been described in detail so as not to unnecessarily obscure aspects of the embodiments.

It will be understood that, although the terms first, second, etc. may be used herein to describe various elements, these elements should not be limited by these terms. These terms are only used to distinguish one element from another. For example, a first sensor could be termed a second sensor, and, similarly, a second sensor could be termed a first sensor, without departing from the scope of the inventive concept.

It will be understood that when an element or layer is referred to as being "on," "coupled to" or "connected to" another element or layer, it can be directly on, directly coupled to or directly connected to the other element or layer, or intervening elements or layers may be present. In contrast, when an element is referred to as being "directly on," "directly coupled to" or "directly connected to" another element or layer, there are no intervening elements or layers present. Like numbers refer to like elements throughout. As used herein, the term "and/or" includes any and all combinations of one or more of the associated listed items.

The terminology used in the description of the inventive concept herein is for the purpose of describing particular embodiments only and is not intended to be limiting of the inventive concept. As used in the description of the inventive concept and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the inventive concept minimize interference and drift caused errors by using a technique that returns a known response from the device as a reference point to correct for the interference and/or drift during operation. The technique includes comparing pre- and post-sample values in the known response and applying that scalar difference to the device output as a correction. This allows for non-laboratory grade sample solutions or media (hereinafter referred to as "sample media") in sample preparation if the reference solution or media (hereinafter referred to as "reference media") is prepared using the same media as the sample media, as any contaminants present in the sample media are accounted for in the reference media.

Embodiments of the inventive concept disclosed herein improve accuracy of measurement compared to normal calibration and single measurement methods executed by ion selective electrodes (ISEs), chemical field effect transistors (CHEMFETs), Hybrid Organic Semiconductor Field Effect Transistors (HOSFETs), and other ion concentration measurement devices or systems for use in non-laboratory settings. Embodiments of the inventive concept provide a reduced time-to-data. In other words, the inventive techniques described herein provide a reduction in the time needed to obtain field samples, perform lab analysis, manage data collation, conduct analysis, and/or conduct action plan production. Not only is the time reduced to obtain the raw data in the field, but also the actionable data provided by the data handling, analysis and return of an action plan is made more efficient. The disclosed techniques provide the capability of making multiple measurements in series, and to have that data transmitted to a database in real time and/or analyzed while subsequent data points are being taken.

Embodiments of the inventive concept enable users to obtain laboratory-quality results in the field in a fraction of the time of a typical lab analysis. Not only does this speed up the decision-making process, it allows more thorough surveys of nitrate flux in heterogeneous media. This can have implications for wastewater, food processing and fisheries industries, and/or itself being a fundamental program of environmental and agronomic research. Direct molecular sensing not only improves upon indirect sensor modalities via a simple, intuitive response (e.g., analyte+sensor=output), but also enables a modular and platformic approach to sensor customization for detection of industrial and environmental analytes of interest.

Figure 1B:
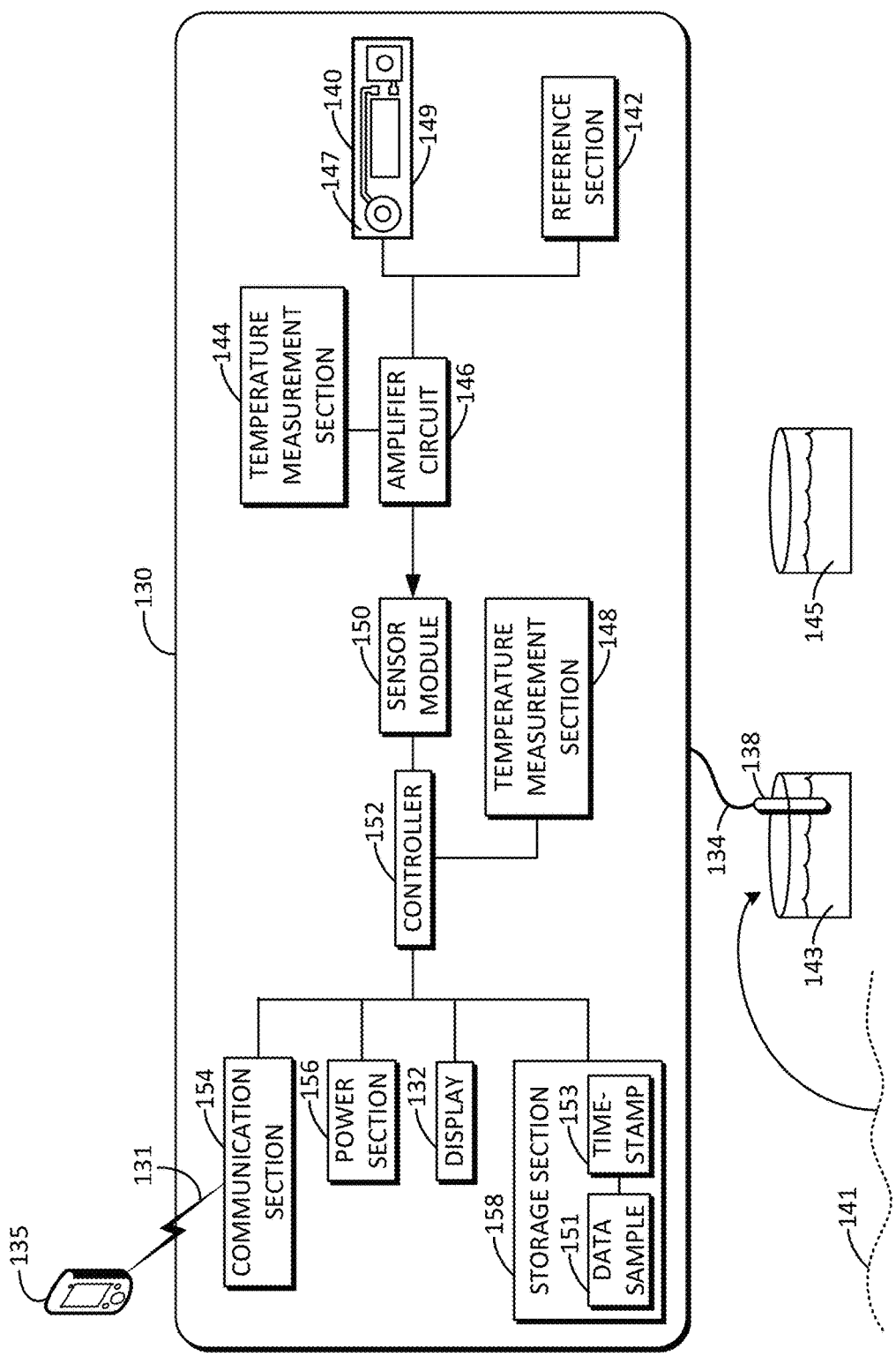
FIG. 1B illustrates an example block diagram including some components of the in-field analysis apparatus of FIG. 1A, in accordance with some embodiments of the present invention.

FIG. 1A illustrates an example portable in-field analysis apparatus 130, in accordance with some embodiments of the present invention. FIG. 1B illustrates an example block diagram including some components of the in-field analysis apparatus 130 of FIG. 1A, in accordance with some embodiments of the present invention. Reference is now made to FIGS. 1A and 1B.

The in-field analysis apparatus 130 can include a display 132 and a control pad 136. In addition, a probe 138 can be coupled to the in-field analysis apparatus 130 via a cable or wire 134. Although shown as being coupled to a top region of the in-field analysis apparatus 130, it will be understood that the in-field analysis apparatus 130 can include a probe 138 coupled via the cable or wire 134 to any suitable region such as a bottom, front, back, or side region. The in-field analysis apparatus 130 can provide data via the display 132 and/or via a wireless transmission 131 to a user's smart phone or mobile device 135, as shown in FIG. 1B. The in-field analysis apparatus 130 can apply a time and/or date stamp 153 to each sample 151 of data. The in-field analysis apparatus 130 can geolocate each data sample 151. Data can be gathered from the in-field analysis apparatus 130 via a wireless connection 131, such as Bluetooth®, near field communication (NFC), WiFi, and/or a cellular network.

As shown in FIG. 1B, the in-field analysis apparatus 130 can include a CHEMFET 140, a reference section 142, a first temperature measurement section 144, and/or an amplifier circuit 146. The in-field analysis apparatus 130 can further include a sensor module 150, a controller 152, a second temperature measurement section 148, a communication section 154, a power section 156, a display 132, and/or a storage section 158.

After soil samples 141 are diluted in water 143, the in-field analysis apparatus 130 can take measurements in the water/soil sample media (e.g., 141/143) and in a separate reference media 145. The reference measurement using the reference media 145 allows for correction for inherent nitrate and/or correction for contamination of the source water 143 used in the field for sample preparation, which bypasses the necessity for bringing deionized water to the field. Alternatively or in addition, the reference measurement allows for correcting any sample-to-sample drift that might accumulate from making measurements in turbid water, otherwise dirtying of the sensor, as further described below. In some embodiments, the controller 152 can correct for the inherent nitrate, the contamination of the sample media, or the sample-to-sample drift. The reference measurement need not be taken while in the field. For example, the reference measurement of the reference media 145 can be taken at a different location such as a laboratory, prior to taking measurements of the sample media in the field.

Data can be delivered in the field for immediate feedback (e.g., diagnostic), stored in the storage section 158, and/or pushed to the cloud via the communication section 154 for incorporation into larger data systems (e.g., on-farm management systems or field mapping). The in-field analysis apparatus 130 can transmit and/or store the data via a wireless connection 131 such as Bluetooth® Low Energy, WiFi, cellular, or the like. Alternatively or in addition, the in-field analysis apparatus 130 can store the data in a removable SD card, a flash drive, and/or via a USB connection for data handling. The storage section 158 can include a non-volatile memory, a volatile memory, a magnetic storage device, an optical storage device, or the like, for storing the data.

The CHEMFET 140 of the in-field analysis apparatus 130 can be, for example, an ion-sensitive field-effect transistor (ISFET). The CHEMFET 140 can include a substrate 147, which can be connected (e.g., wirebonded) to a printed circuit board (PCB) 149, and other various components disposed in or on the substrate 147. The CHEMFET 140 can be coupled to the reference section 142 and to the amplifier circuit 146. Feedback from the amplifier circuit 146 can cause an electrical current to remain substantially constant to allow measurement of a changing gate voltage of the CHEMFET 140. An amplified output voltage from the amplifier circuit 146 is an indicator of the quantity of nitrate levels in the sample media and/or the reference media. The PCB 149, the substrate 147, and other various components of the CHEMFET 140 can be encapsulated by an impervious electrically insulative resin, except for an exposed gate region. Onto the exposed gate region can be cast (e.g., by spin or drop coating) membrane material. The exposed gate region can come into direct contact with the sample media (e.g., 141/143) and/or with the reference media (e.g., 145). For example, the CHEMFET 140 can be embedded into the probe 138 for easy access and sampling of the sample media (e.g., 141/143) and/or the reference media (e.g., 145). In some embodiments, the sensor module 150 is embedded into the probe 138.

The reference media (e.g., 145) can include a known ion concentration. In some embodiments, a range of reference media can be provided to suit ranges of ion concentrations that can be updated by the user. The known ion concentration can be of any value that corresponds to one of the reference media. The reference measurement need not be taken while in the field. For example, the reference measurement of the reference media 145 can be taken at a different location such as a laboratory, prior to taking measurements of the sample media in the field. The in-field analysis apparatus 130 can measure ion concentration of the sample media (e.g., 141/143) using the probe 138, the CHEMFET 140, and/or other components of the in-field analysis apparatus 130, and can obtain an electromotive force value. It will be understood that the actual measurement process can be any suitable process to obtain the electromotive force as long as it is consistent between the sample media (e.g., 141/143) and the reference media (e.g., 145), and allows equilibration of the in-field analysis apparatus 130.

The reference section 142 may store known ion concentrations corresponding to one or more reference media 145. For example, the reference section 142 can store a range of known reference media ion concentrations, which can be updated by a user of the in-field analysis apparatus 130. The temperature measurement section 144 can be coupled to the amplifier circuit 146. In some embodiments, the temperature measurement section 144 can be embedded in the probe 138. The temperature measurement section 144 can include a temperature sensor to sense the temperature of the sample media (e.g., 141/143) and the reference media (e.g., 145).

The sensor module 150 of the in-field analysis apparatus 130 can receive ion concentration information and/or other sensed information from the amplifier circuit 146, the CHEMFET 140, and/or the temperature measurement section 144. In some embodiments, the sensor module 150 can include the amplifier circuit 146, the CHEMFET 140, the reference section 142, and/or the temperature measurement section 144. The sensor module 150 can transmit the gathered information to the controller 152, which can process the sensed information. The controller 152 can be coupled to a second temperature measurement section 148, which can be embedded within the in-field analysis apparatus 130. The second temperature measurement section 148 can include a temperature sensor to sense the temperature of the surrounding environment. The power section 156 can include, for example, a battery within a battery compartment and/or an external wire jack for providing power to the in-field analysis apparatus 130. The display 132 can visibly present sensed information such as the ion concentration of the sample media (e.g., 141/143). Alternatively or in addition, the display 132 can visibly present information stored in the storage section 158, such as data samples 151, timestamp information 153, or the like. The control pad 136 can be used by the user to navigate the information presented on the display 132.

Figure 1C:
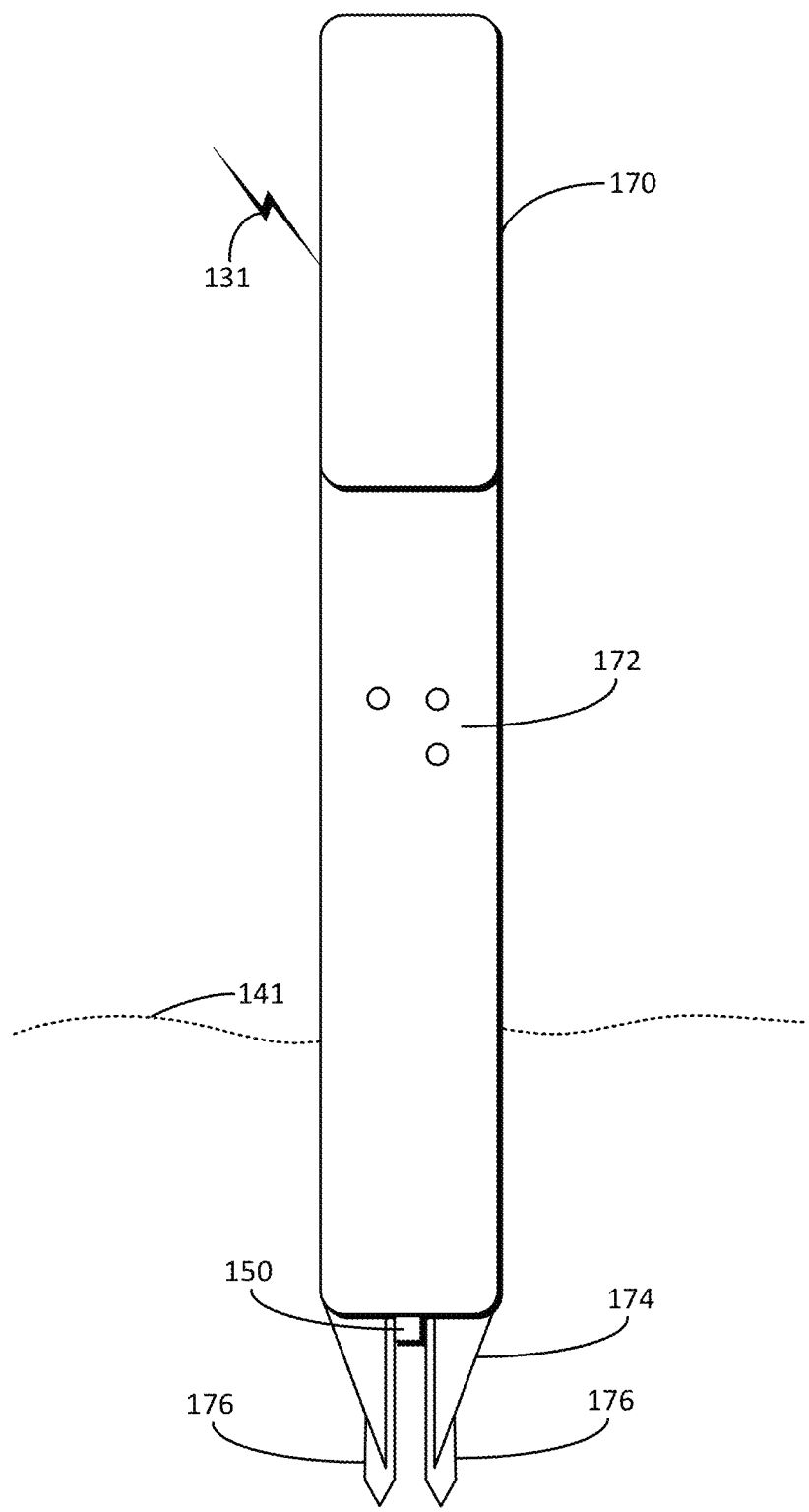
FIG. 1C illustrates an example portable in-soil measurement apparatus, in accordance with some embodiments of the present invention.
Figure 1D:
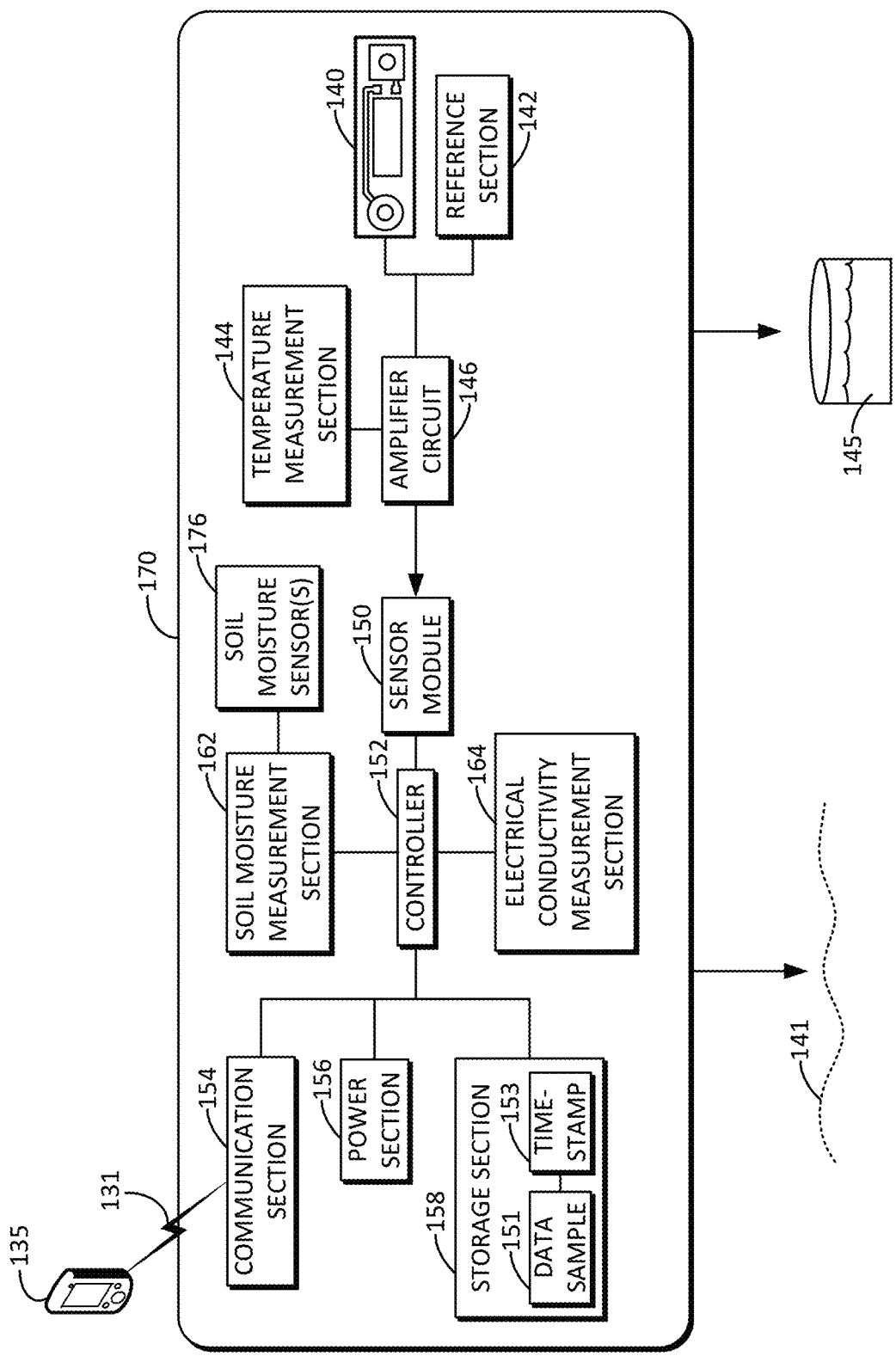
FIG. 1D illustrates an example block diagram including some components of the in-soil measurement apparatus of FIG. 1C, in accordance with some embodiments of the present invention.

FIG. 1C illustrates an example portable in-soil measurement apparatus 170, in accordance with some embodiments of the present invention. FIG. 1D illustrates an example block diagram including some components of the in-soil measurement apparatus 170 of FIG. 1C, in accordance with some embodiments of the present invention. Reference is now made to FIGS. 1C and 1D.

The in-soil measurement apparatus 170 includes a form factor that allows for insertion directly into soil 141, thereby bypassing the need for sample preparation. The in-soil measurement apparatus 170 can communicate via a wireless connection 131 to a user's smart phone or mobile device 135. In some embodiments, the in-soil measurement apparatus 170 need not include an onboard display to avoid breakage during soil insertion or to reduce cost. In some embodiments, the in-soil measurement apparatus 170 can include a reinforced onboard display. The in-soil measurement apparatus 170 can include a soil moisture and/or resistivity measurement section 162 to correct for differences in measured sample water content, which can provide parts per million nitrate data.

The in-soil measurement apparatus 170 can include one or more prongs 174 disposed toward the bottom of the apparatus. One or more soil moisture sensors 176 can be attached to the one or more prongs 174 for insertion into the soil 141. A sensor module 150 can be housed perpendicularly between the prongs 174, up against the bottom of the in-soil measurement apparatus 170. The in-soil measurement apparatus 170 can include one or more light emitting diode (LED) indicators 172, which can indicate status information to the user. For example, the status information can include a ready indicator, a measurement complete indicator, a power on indicator, or the like. It will be understood that the in-soil measurement apparatus 170 can be of any suitable length, and can include a tool to insert the device to a given depth for analysis.

As shown in FIG. 1D, the in-soil measurement apparatus 170 can include a CHEMFET 140, a reference section 142, a temperature measurement section 144, and/or an amplifier circuit 146. The in-soil measurement apparatus 170 can further include a sensor module 150, a controller 152, a soil moisture measurement section 162, an electrical conductivity measurement section 164, a communication section 154, a power section 156, and/or a storage section 158. Some of the components of the in-soil measurement apparatus 170 are the same or similar to components of the in-field analysis apparatus 130, and therefore, a detail description of such same or similar components is not necessarily repeated.

Since the in-soil measurement apparatus 170 includes a form factor that allows for insertion directly into the soil 141, sample preparation of sample media need not be performed. The reference media 145 can include a known ion concentration. In some embodiments, a range of reference media can be provided to suit ranges of ion concentrations that can be updated by the user. The known ion concentration can be of any value that corresponds to one of the reference media. The reference measurement need not be taken while in the field. For example, the reference measurement of the reference media 145 can be taken at a different location such as a laboratory, prior to taking measurements of the sample media in the field. The in-soil measurement apparatus 170 can directly measure ion concentration of the soil 141 by insertion of the one or more prongs 174 into the soil 141. The in-soil measurement apparatus 170 can use the CHEMFET 140 and/or other components of the in-soil measurement apparatus 170 to make the measurement, and can obtain an electromotive force value. It will be understood that the actual measurement process can be any suitable process to obtain the electromotive force as long as it is consistent between the soil 141 and the reference media 145, and allows equilibration of the in-soil measurement apparatus 170. In some embodiments, the controller 152 can correct for inherent nitrate or the sample-to-sample drift.

The reference section 142 may store known ion concentrations corresponding to one or more reference media 145. For example, the reference section 142 can store a range of known reference media ion concentrations, which can be updated by a user of the in-soil measurement apparatus 170. The temperature measurement section 144 can be coupled to the amplifier circuit 146. In some embodiments, the temperature measurement section 144 can be embedded in the in-soil measurement apparatus 170. The temperature measurement section 144 can include a temperature sensor to sense the temperature of the soil 141 and/or the reference media 145.

The sensor module 150 of the in-soil measurement apparatus 170 can receive ion concentration information and/or other sensed information from the amplifier circuit 146, the CHEMFET 140, and/or the temperature measurement section 144. In some embodiments, the sensor module 150 can include the amplifier circuit 146, the CHEMFET 140, the reference section 142, and/or the temperature measurement section 144. The sensor module 150 can transmit the gathered information to the controller 152, which can process the sensed information. The controller 152 can be coupled to a soil moister measurement section 162, which can measure moisture within the soil 141. For example, the one or more soil moisture sensors 176 can gather soil moisture information and transmit the information to the soil moisture measurement section 162, which can be processed by the controller 152. Moreover, the controller 152 can be coupled to an electrical conductivity measurement section 164, which can measure electrical conductivity within the soil 141. The power section 156 can include, for example, a battery within a battery compartment and/or an external wire jack for providing power to the in-soil measurement apparatus 170.

Figure 1E:
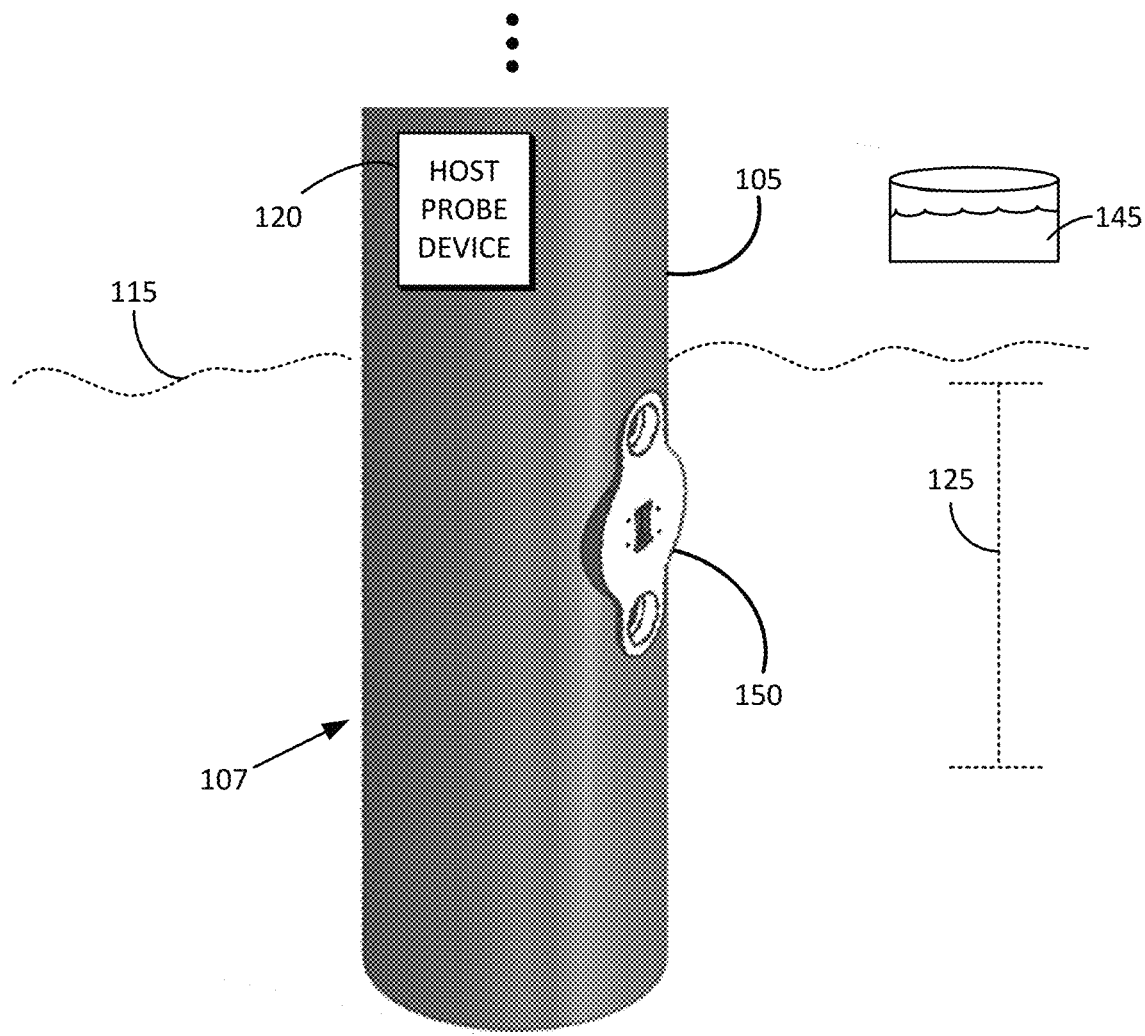
FIG. 1E illustrates an example in-soil monitoring apparatus, in accordance with some embodiments of the present invention.
Figure 1F:
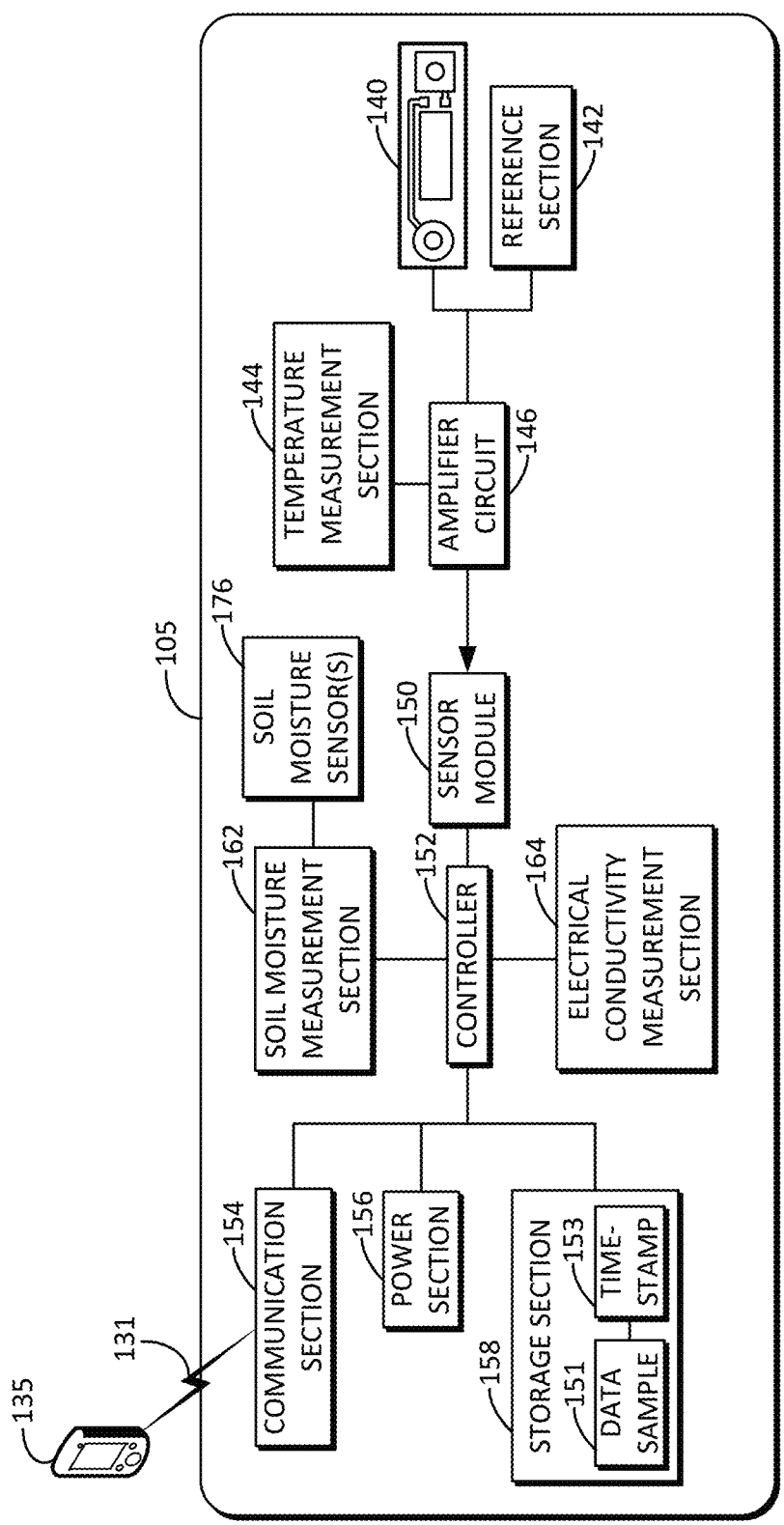
FIG. 1F illustrates an example block diagram including some components of the in-soil monitoring apparatus of FIG. 1E, in accordance with some embodiments of the present invention.

FIG. 1E illustrates an example in-soil monitoring apparatus 105, in accordance with some embodiments of the present invention. FIG. 1F illustrates an example block diagram including some components of the in-soil monitoring apparatus 105 of FIG. 1E, in accordance with some embodiments of the present invention. Reference is now made to FIGS. 1E and 1F.

Distinct from a measurement-only or hand-held device, the in soil monitoring apparatus 105 can monitor soil conditions in real time and/or continuously. The in-soil monitoring apparatus 105 is generally an in-ground device. The in-soil monitoring apparatus 105 can be housed in a permanent stake or outer housing 107, and can include long range communications at the surface.

The sensor module 150 can be installed and/or contained partially or fully into the outer housing 107 for insertion into the field ground soil 115. The outer housing 107 can include one or more sensor modules 150. The outer housing 107 can be made of, for example, a polyvinyl chloride (PVC) pipe or any other suitable probe material capable of receiving the sensor module 150 and capable of being inserted into the field ground soil 115.

The sensor module 150 can be included within or otherwise interface with the host probe device 120, which can be contained partially or fully within the outer housing 107. The sensor module 150 can be separate from the host probe device 120. In other words, the host probe device 120 can be external to the sensor module 150. The sensor module 150 can wirelessly interface with the host probe device 120 using one or more transceivers (e.g., near field communications chips (NFC)) for data transfer to and from the host probe. In some embodiments, the communication section 154 includes the one or more NFC chips. The wireless feature avoids breaking the seal between the field ground soil 115 and internal electronics in both the sensor module 150 and the host probe 120 any more than necessary, and allows for easy access for recalibration and/or replacement of the nitrate sensor and/or ion concentration measurement portion. In some embodiments, the sensor module 150 can communicate directly with a smart phone (e.g., 235 of FIG. 2), tablet (e.g., 240 of FIG. 2), or other suitable mobile device, via the NFC, Bluetooth® protocol, cellular link, and/or other suitable short-range or long-range wireless interface. In some embodiments, the host probe device 120 can provide electrical conductivity, pH data, and/or temperature data that the sensor data can be calibrated against. The host probe device 120 can include one or more NFC chips for receiving data or instructions from and/or sending data or instructions to the one or more NFC chips of the sensor module 150 or communication section 154. The host probe device 120 can include a long-range communication section, such as a cellular transceiver, to transmit data collected by the in-soil monitoring apparatus 105, or to receive information or instructions for the in-soil monitoring apparatus 105.

In some embodiments, the long-range transceiver can be located within the outer housing 107 (e.g., within the host probe device 120), but above a ground level of the soil 115. The NFC chip of the sensor module 150 or the communication section 154 can communicate with the NFC chip of the host probe device 120 over a short-range communication link, and the host probe device 120 can communicate with an external computing device (e.g., smart phone (e.g., 235 of FIG. 2), tablet (e.g., 240 of FIG. 2), or other suitable mobile device, over a long-range communication link.

For example, a first NFC chip can be coupled to the controller 152. The first NFC chip can transmit one or more data samples (e.g., 151) and associated information over a short-range communication link. A second NFC chip can be embedded in the host probe device 120 located above a ground level of the soil 115 within the outer housing 107. The second NCF chip can receive the one or more data samples from the first NFC chip. The host probe device 120 can include a long-range communications section located above the ground level within the outer housing 107, and can wirelessly transmit the one or more data samples 151 over a long-range communication link.

Multiple probe bodies 105, along with associated sensor modules 150, can be installed in field soils at varying depths, typically in the root zone 125 (i.e., top of root to bottom of root). In other words, the sensor module 150 can be installed at a depth within the field ground soil that is between a top of the root zone 125 and a bottom of the root zone 125. In addition, the outer housing 107 can be installed below the root zone 125. Alternatively, a single outer housing 107 can include multiple sensor modules 150, each sensor module 150 spaced apart within the root zone 125, and/or below the root zone 125. This allows for data collection, by a first sensor module 150, of the nitrate gradient and/or ion concentration measurement in the field ground soil in the active area of plant uptake 125, and a second sensor module (not shown) below the active area 125 that serves as an alert system when the field is either over-fertilized, over watered, and/or the soil nitrate is washing below the reach of the plants' roots.

As shown in FIG. 1F, the in-soil monitoring apparatus 105 can include a CHEMFET 140, a reference section 142, a temperature measurement section 144, and/or an amplifier circuit 146. The in-soil monitoring apparatus 105 can further include a sensor module 150, a controller 152, a soil moisture measurement section 162, an electrical conductivity measurement section 164, a communication section 154, a power section 156, and/or a storage section 158. Some of the components of the in-soil monitoring apparatus 105 are the same or similar to components of the in-soil measurement apparatus 170, and therefore, a detail description of such same or similar components is not necessarily repeated.

Since the in-soil monitoring apparatus 105 is designed to be permanently or semi-permanently inserted into the soil 115, sample preparation of sample media need not be performed. The reference media 145 can include a known ion concentration. In some embodiments, a range of reference media can be provided to suit ranges of ion concentrations that can be updated by the user. The known ion concentration can be of any value that corresponds to one of the reference media. The reference measurement need not be taken while in the field. For example, the reference measurement of the reference media 145 can be taken at a different location such as a laboratory, prior to taking measurements of the sample media in the field. The in-soil monitoring apparatus 105 can directly measure ion concentration of the soil 115 by direct contact of the sensor module 150 with the soil 115. The in-soil monitoring apparatus 105 can use the CHEMFET 140 and/or other components of the in-soil monitoring apparatus 105 to make the measurement, and can obtain an electromotive force value. It will be understood that the actual measurement process can be any suitable process to obtain the electromotive force as long as it is consistent between the soil 115 and the reference media 145, and allows equilibration of the in-soil monitoring apparatus 105.

The reference section 142 may store known ion concentrations corresponding to one or more reference media 145. For example, the reference section 142 can store a range of known reference media ion concentrations, which can be updated by a user of the in-soil monitoring apparatus 105. The temperature measurement section 144 can be coupled to the amplifier circuit 146. In some embodiments, the temperature measurement section 144 can be embedded in the in-soil monitoring apparatus 105. The temperature measurement section 144 can include a temperature sensor to sense the temperature of the soil 115 and/or the reference media 145.

The sensor module 150 of the in-soil monitoring apparatus 105 can receive ion concentration information and/or other sensed information from the amplifier circuit 146, the CHEMFET 140, and/or the temperature measurement section 144. In some embodiments, the sensor module 150 can include the amplifier circuit 146, the CHEMFET 140, the reference section 142, and/or the temperature measurement section 144. The sensor module 150 can transmit the gathered information to the controller 152, which can process the sensed information. The controller 152 can be coupled to a soil moister measurement section 162, which can measure moisture within the soil 115. For example, one or more soil moisture sensors 176 can gather soil moisture information and transmit the information to the soil moisture measurement section 162, which can be processed by the controller 152. Moreover, the controller 152 can be coupled to an electrical conductivity measurement section 164, which can measure electrical conductivity within the soil 115. The power section 156 can include, for example, a battery within a battery compartment and/or an external wire jack for providing power to the in-soil monitoring apparatus 105.

Figure 2:
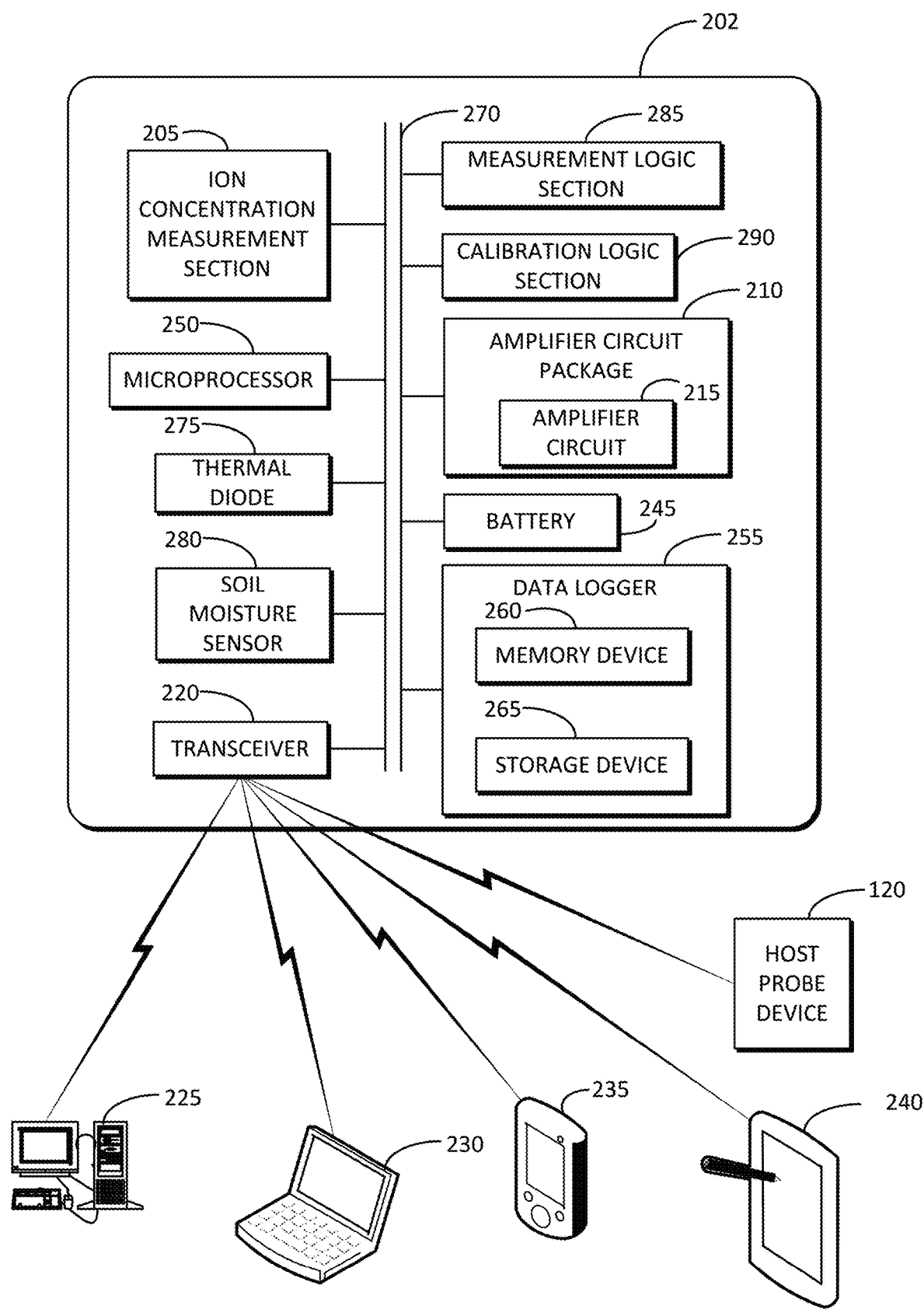
FIG. 2 illustrates an example block diagram of a sensor module including various components disposed therein, within a larger system of external computing devices, in accordance with some embodiments of the present invention.

FIG. 2 illustrates a schematic system block diagram of a measurement module 202, which can be included in the in-field analysis apparatus 130 (of FIGS. 1A-1B), the in-soil measurement apparatus 170 (of FIGS. 1C-1D), and/or the in-soil monitoring apparatus 105 (of FIGS. 1E-1F). It will be understood that some or all of the components of the measurement module 202 can be included in the various apparatuses 130, 170, and/or 105. In other words, all of the components of the measurement module 202 need not be present in each of the various apparatuses 130, 170, and/or 105.

The measurement module 202 can include an ion concentration measurement section 205, such as one or more ion ISEs, CHEMFETs, HOSFETs, and/or other suitable ion concentration measurement devices. The measurement module 202 can include a measurement logic section 285, as described in detail below. The measurement module 202 can include a calibration logic section 290, as also described in detail below. The measurement module 202 can include an amplifier circuit package 210 including an amplifier circuit 215.

In addition, the measurement module 202 can contain a transceiver 220 for interfacing with external and/or remote devices such as computer 225, laptop 230, smart phone 235, tablet 240, and/or the host probe device 120. For example, a user of the computer 225, laptop 230, smart phone 235, and/or tablet 240, can access ion concentration measurement information by communicating with the transceiver 220 via wires and/or wirelessly. The transceiver 220 can be a near field communications chip (NFC). By way of another example, the host probe device 120 can be partially or fully contained within a same probe (not shown) as the measurement module 202. One or more components within the measurement module 202 can communicate with one or more components within the host probe device 120 via wires and/or wirelessly.

The measurement module 202 can further include a battery 245, a microprocessor 250, and/or data logger 255. The data logger 255 can include a memory device 260 and/or other suitable storage device 265 for storing ion concentration measurement information over a period of time. Two or more of the various components within the measurement module 202 can be communicatively coupled to each other via bus 270.

A single measurement module (e.g., 202) can include the ion concentration measurement section 205, the measurement logic section 285, the calibration logic section 290, the amplifier package 210, the data logger or data acquisition unit 255, and/or the transceiver 220, for connection to a personal computer 225 and/or other suitable external computing device (e.g., 230, 235, 240). The measurement module 202 can include external electrical conductivity and/or connectivity, for example, such as an external electrical port for powering the module 202. The measurement module 202 can include a thermal diode 275, and/or a soil moisture sensor 280, which can be more useful for home and garden use. The thermal diode 275 can convert a heat difference into electric power, which can be used by the measurement module 202. The soil moisture sensor 280 can sense a moisture content within the sample media (e.g., 141/143 of FIG. 1B), the reference media (e.g., 145 of FIG. 1B), and/or directly in the soil (e.g., 141 of FIG. 1D).

The ion concentration measurement section 205 can measure ion concentration in the sample media (e.g., 141/143 of FIG. 1B), the reference media (e.g., 145 of FIG. 1B), and/or directly in the soil (e.g., 141 of FIG. 1D). The measurement logic section 285 can be coupled to the ion concentration measurement section 205, and may improve the accuracy or control of the ion concentration measurement. The calibration logic section 290 can calibrate the ion concentration measurement section 205 and/or nitrate sensor. Feedback from the amplifier circuit 215 can cause an electrical current to remain substantially constant to allow measurement of a changing gate voltage of a CHEMFET (e.g., 140 of FIG. 1B). An amplified output voltage from the amplifier circuit 215 can be an indicator of the quantity of nitrate levels in the sample media (e.g., 141/143 of FIG. 1B), the reference media (e.g., 145 of FIG. 1B), and/or directly in the soil (e.g., 141 of FIG. 1D). The microprocessor 250 can process data samples and other information provided by any one or all of the other components of the measurement module 202.

Figure 3:
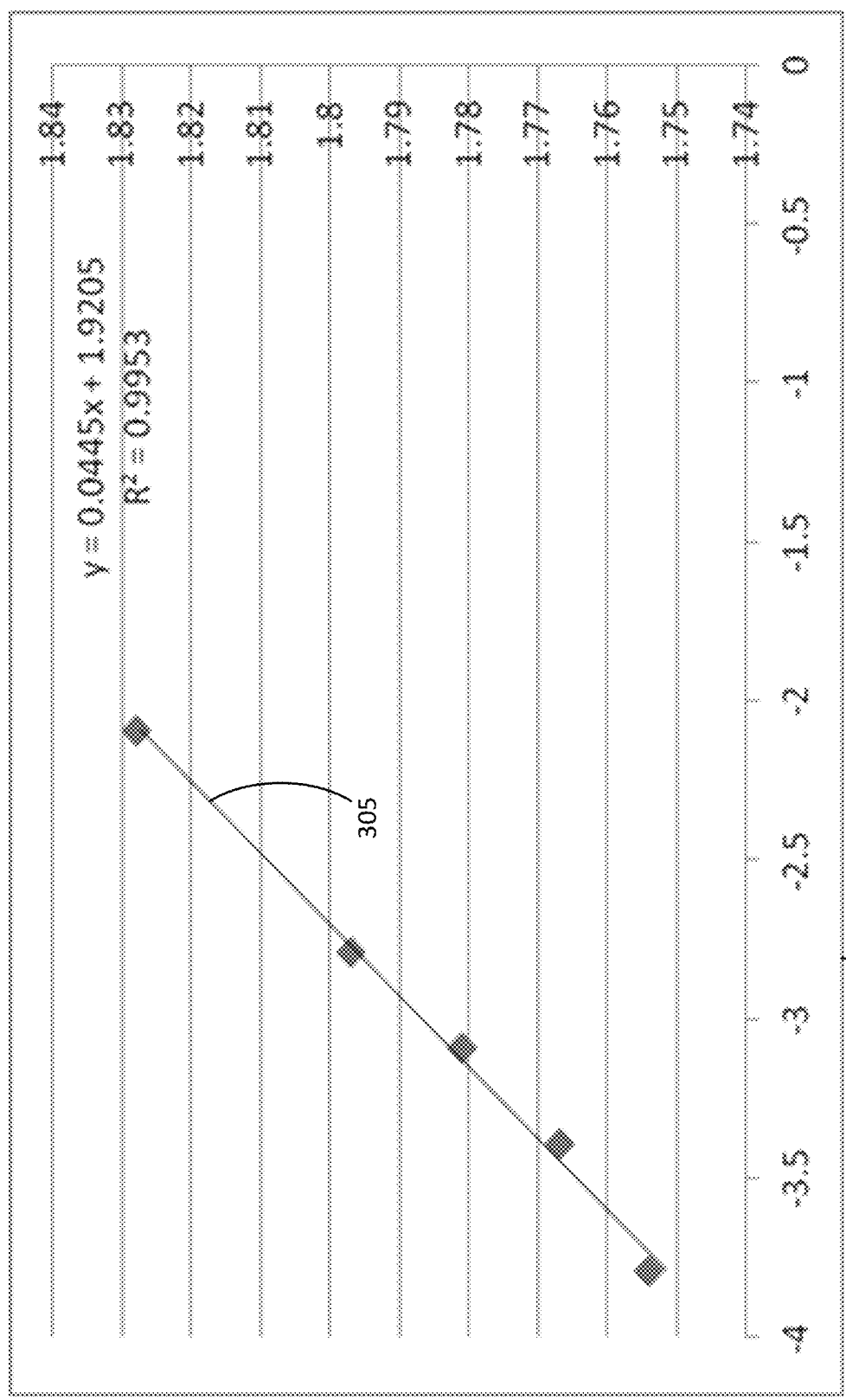
FIG. 3 illustrates an example of a calibration plot used for calibrating a sensor module and/or a measurement module in accordance with some embodiments of the present invention.
Figure 4:
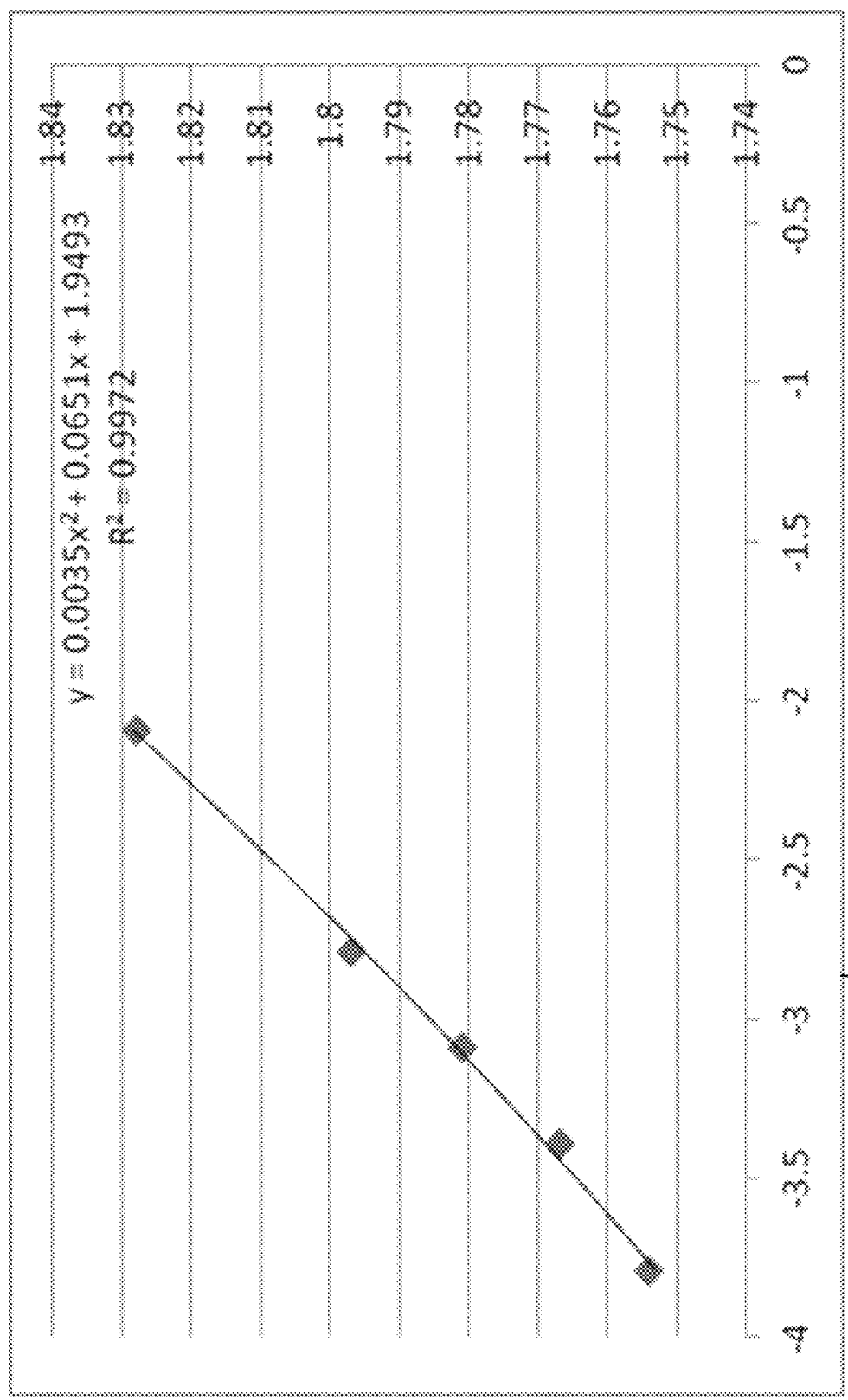
FIG. 4 illustrates another example of a calibration plot used for calibrating the sensor module in accordance with some embodiments of the present invention.

FIG. 3 illustrates an example of a calibration plot 300 useful for calibrating a sensor module (e.g., 150 of FIG. 1B) and/or a measurement module (e.g., 202 of FIG. 2) in accordance with some embodiments of the present invention. FIG. 4 illustrates another example of a calibration plot 400 useful for calibrating the sensor module or the measurement module in accordance with some embodiments of the present invention.

Referring to FIGS. 2 through 4, the sensor module (e.g., 150 of FIG. 1B) and/or the measurement module (e.g., 202 of FIG. 2) can be calibrated using the calibration logic section 290 at the factory prior to being used in the field. Alternatively or in addition, the sensor module (e.g., 150 of FIG. 1B) and/or the measurement module (e.g., 202 of FIG. 2) can be calibrated in the field, for example, by a user through menu selections, for example, via the display (e.g., 132 of FIG. 1A), or through menu selections available through a remotely connected device (e.g., computer 225, laptop 230, smart phone 235, and/or tablet 240 of FIG. 2). The calibration logic section 290 can receive the instructions and/or store one or more calibration values. Calibration reduces error propagation in ion concentration measurement processes disclosed herein.

As shown in FIG. 3, the calibration plot 300 can provide a sensitivity slope M as shown at 305, which can be represented in units of Volts per decade of concentration. The X axis can be represented in units of a decade. A decade can be equivalent to Log(known concentration/ion concentration), where the known concentration can be the known ion concentration of a known reference media (e.g., 145 of FIG. 1B) in parts per million (ppm), and the ion concentration can be the ion concentration of sample media (e.g., 141/143 of FIG. 1B). The Y axis can be represented in Volts. Thus, the calibration plot 300 can be a plot of the measured electromotive force (Y axis) versus the log of the ion concentration (X axis). The sensitivity slope M, as shown at 305, can be calculated as a linear line of best fit for the calibration plot 300. The sensitivity slope M can be determined when a calibration is performed in the sensor module (e.g., 150 of FIG. 1B), in the measurement module (e.g., 202 of FIG. 2), and/or in an external device (e.g., via the cloud). A factor calibration, for example, to determine the sensitivity slope M, can be performed once. The sensitivity slope M can be stored in the sensor module (e.g., 150 of FIG. 1B), in the measurement module (e.g., 202 of FIG. 2), and/or in an external device (e.g., via the cloud). The user can update this calibration with a user calibration, but can always return to the original default factory calibration.

For example, the following points can be plotted in the calibration plot 300:

| X | Y |
|---|---|
| −3.79239 | 1.754 |
| −3.39445 | 1.767 |
| −3.09342 | 1.781 |

-continued

| X | Y |
|---|---|
| −2.79239 | 1.797 |
| −2.09342 | 1.828 |

It will be understood that other suitable points can be plotted, which can help determine the sensitivity slope M at time of calibration. The data points can be obtained using the sensor module (e.g., 150 of FIG. 1B) and/or the measurement module 202 (e.g., of FIG. 2). In the example shown in FIG. 3, the sensitivity slope M is equal to 0.0445 Volts/decade. The sensitivity slope M as shown at 305 of calibration plot 300 can be obtained using a linear line of best fit, for example, using the linear equation form of Y=M*X+B. It will be understood that other sensitivity slopes can be obtained besides the one shown.

Referring now to the ion concentration measurement section 205 and the measurement logic section 285 (of FIG. 2), a reference media (e.g., 145 of FIG. 1B) can be created or obtained, which contains a known ion concentration. A range of reference media can be provided to suit ranges of ion concentrations that can be updated by the user. The known ion concentration can be of any value that corresponds to one of the reference media. The sensor module (e.g., 150 of FIG. 1B) and/or the measurement module 202 (e.g., of FIG. 2) can measure ion concentration of a sample media (e.g., 141/143 of FIG. 1B) using the ion concentration measurement section 205. The measurement logic section 285 can obtain a first electromotive force value. It will be understood that the actual measurement process can be any suitable process to obtain the electromotive force as long as it is consistent between the sample media (e.g., 141/143 of FIG. 1B) and the reference media (e.g., 145 of FIG. 1B), and allows equilibration of the measurement device (e.g., measurement module 202) or system.

The sensor module (e.g., 150 of FIG. 1B) and/or the measurement module 202 (e.g., of FIG. 2) can measure ion concentration of a reference media (e.g., 145 of FIG. 1B) from among the various reference media using the ion concentration measurement section 205, and the measurement logic section 285 can obtain a second electromotive force value. The measurement logic section 285 can determine a value of the ion concentration of the sample media (e.g., 141/143 of FIG. 1B) based at least on the first electromotive force value, the second electromotive force value, and the sensitivity slope M. More specifically, the measurement logic section 285 can determine the value of the ion concentration of the sample media (e.g., 141/143 of FIG. 1B) according to the following formula:

$$\text{Value} = \text{Ion} * 10^{\left[\frac{\text{Read}-\left(\text{Ref}-\left(\text{Slope}*\text{Log}\left(\frac{\text{Known}}{\text{Ion}}\right)\right)\right)}{\text{Slope}}\right]},$$

where:
value=value of the ion concentration of the sample media;
Ion=weight of ion to be measured multiplied by one thousand (1000);
Read=electromotive force obtained during measurement of the sample media;
Ref=electromotive force obtained during measurement of the reference media;
Slope=slope of the sensitivity slope M; and Known=the ion concentration of the known reference media in parts per million (ppm).

The Ion value is a constant that can be set by a formula weight of the ion of interest. For example, when the Ion is Nitrate, the formula weight of the ion is 62 grams/mol, and thus, the Ion value is 62,000. The Ion value can be updated or changed for any other suitable analyte. The Known value is the measurement of the ion concentration of the reference media. The measurement logic section 285 can determine the value based on the above formula after the analog measurement data (e.g., milli-volt output) is converted to digital data, the data points gathered, and fed into the value determination formula above. It will be understood that the measurement logic section 285 can exist external to the measurement module 202 (e.g., within the computer 225, tablet 240, etc. of FIG. 2).

In some embodiments, the first electromotive force value, the second electromotive force value, and the sensitivity slope M can be transmitted to a remote database, for example, to the computer 225, either via wires or wirelessly. In some embodiments, some of the data (e.g., sensitivity slope M) can already exist on the remote database, for example, having been previously gathered or determined. Once the Known, Ion, Read, Ref, and Slope values are obtained in some fashion, for example as described herein, and are accessible from either the measurement module 202 or the remote database, or both, then the value of ion concentration in the sample media can be accurately determined.

FIG. 4 shows another example of a calibration plot 400 and corresponding polynomial coefficients. The polynomial coefficients of the calibration plot 400 can be obtained using a polynomial fit, for example, using the polynomial equation form of $Y=Ax^2+Bx+C$. During the calibration, a polynomial fit of any order can be used. This technique changes the formula used to determine the value of the ion concentration in the sample media due to how the calibration curve is shifted. Polynomial coefficients can be found instead of the sensitivity slope M in the linear form. For example, with reference to FIG. 4, the polynomial coefficients are $A=0.0035$, $B=0.0651$, $C=1.9493$. It will be understood that other suitable coefficients can be used. The following equations are for determining the corrected ion concentration value when using a polynomial fit.

The sensor module (e.g., 150 of FIG. 1B) and/or the measurement module 202 (e.g., of FIG. 2) can measure ion concentration of a reference media (e.g., 145 of FIG. 1B) from among the various reference media using the ion concentration measurement section 205, and the measurement logic section 285 can obtain a second electromotive force value. The measurement logic section 285 can determine a value of the ion concentration of the sample media based at least on the first electromotive force value, the second electromotive force value, and the polynomial coefficients. More specifically, the measurement logic section 285 can determine the value of the ion concentration of the sample media according to the following formulas:

$$Value = Ion * 10^{\left[\frac{-B^2+\sqrt{B^2-4A((C-Shift)-Read)}}{2A}\right]}; \text{ and}$$

$$Shift = \left(\left(A*\left(\log\left(\frac{Known}{Ion}\right)\right)^2\right) + B*\log\left(\frac{Known}{Ion}\right) + C\right) - Ref,$$

where:

Value=value of the ion concentration of the sample media;

Ion=weight of ion to be measured multiplied by one thousand (1000);

Read=electromotive force obtained during measurement of the sample media;

Ref=Electromotive force obtained during measurement of the reference media;

A=A Coefficient in the polynomial equation form of $Y=Ax^2+Bx+C$;

B=B Coefficient in the polynomial equation form of $Y=Ax^2+Bx+C$;

C=C Coefficient in the polynomial equation form of $Y=Ax^2+Bx+C$; and

Known=the ion concentration of the known reference media in (ppm).

As with the previous embodiment, the Ion value is a constant that can be set by a formula weight of the ion of interest. For example, when the Ion is Nitrate, the formula weight of the ion is 62 grams/mol, and thus, the Ion value is 62,000. The Ion value can be updated or changed for any other suitable analyte. The Known value is the measurement of the ion concentration of the reference media. The measurement logic section 285 can determine the value based on the above formula after the analog measurement data (e.g., milli-volt output) is converted to digital data, the data points gathered, and fed into the value determination formula above. It will be understood that the measurement logic section 285 can exist external to the measurement module 202 (e.g., within the computer 225, tablet 240, etc. of FIG. 2).

In some embodiments, the first electromotive force value, the second electromotive force value, and the polynomial coefficients can be transmitted to a remote database, for example, to the computer 225, either via wires or wirelessly. In some embodiments, some of the data (e.g., polynomial coefficients) can already exist on the remote database, for example, having been previously gathered or determined. Once the Known, Ion, Read, Ref, and Coefficient values are obtained in some fashion as described herein, and are accessible from either the measurement module 202 or the remote database, or both, then the value of ion concentration in the sample media can be accurately determined.

Figure 5:
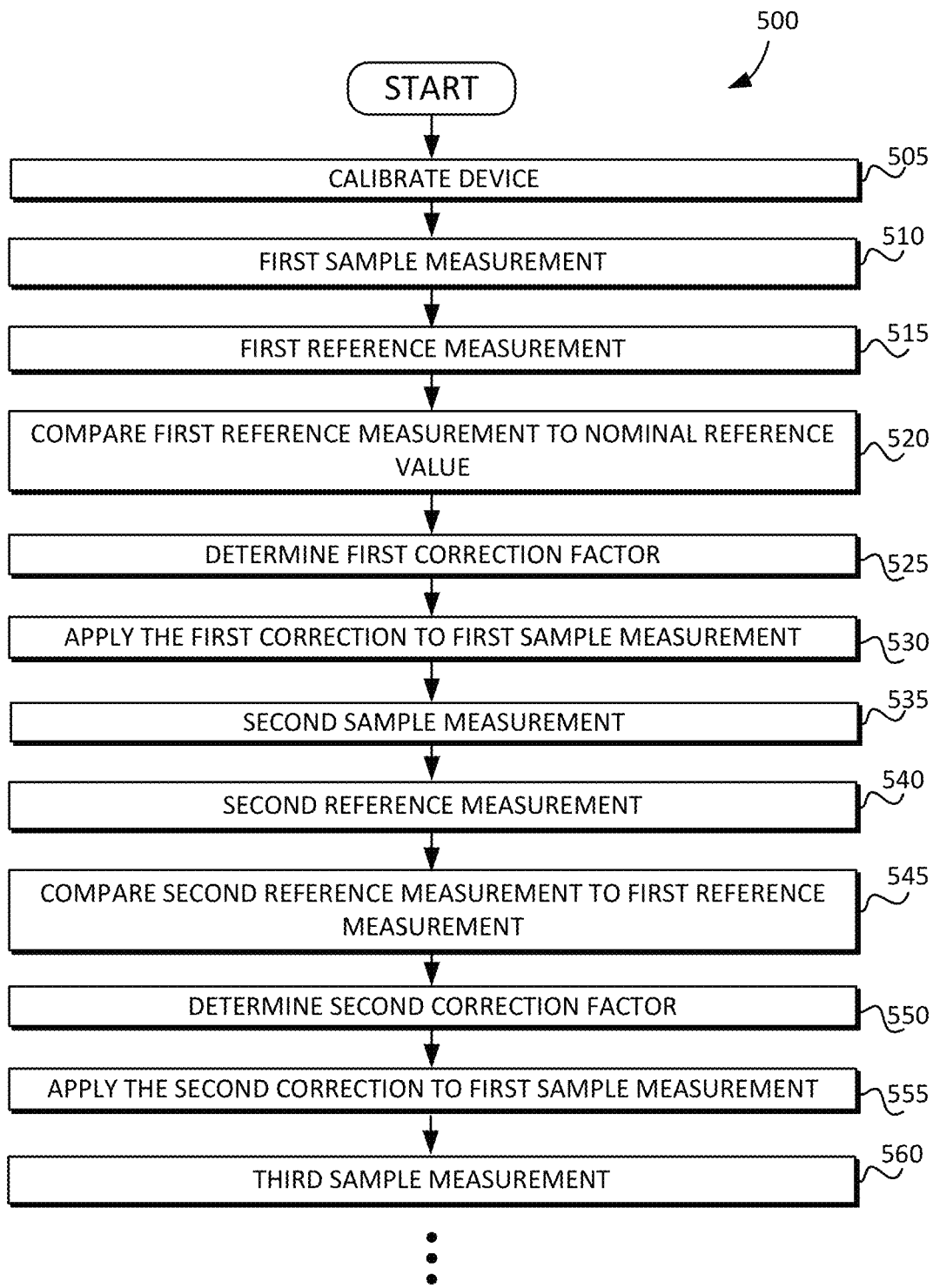
FIG. 5 is a flow diagram illustrating a technique for securing a membrane using impervious electrically insulative resin, in accordance with some embodiments of the present invention.

FIG. 5 is a flow diagram illustrating another technique 500 for measuring ion concentration with a standard deviation correction. The flow begins at 505, where a device (e.g., sensor module 150 or measurement module 202) can be calibrated, for example, using the calibration logic section 290. At 510, a first sample measurement can be taken from a sample media. At 515, a first reference measurement can be taken from a reference media. At 520, the measurement logic section (e.g., 285) can compare the first reference measurement to a nominal reference value. At 525, the measurement logic section 285 can determine a first correction factor. In some embodiments, the first correction factor can be dependent on the comparison of the first reference measurement to the nominal reference value. At 530, the measurement logic section 285 can apply the first correction factor to the first sample measurement. At 535, a second sample measurement can be taken from the sample media. At 540, a second reference measurement can be taken from the reference media. At 545, the measurement logic section 285 can compare the second reference measurement to the first reference measurement. At 550, the measurement logic section 285 can determine a second correction factor. In some embodiments, the second correction factor can be dependent on the comparison of the second reference measurement to the first reference measurement. At 555, the measurement logic section 285 can apply the second correction factor to the first sample measurement.

At 560, a third sample measurement can be taken from the sample media. The flow can continue for N number of samples taken from the sample media. In other words, similar steps to those of 535-555 can be repeated for the third sample measurement, a fourth sample measurement, and so forth. For example, in the case of the third sample measurement, a similar step to step 545 can compare the third reference measurement to the second reference measurement, to determine a third correction factor, which can be applied to the first sample measurement. It will be understood that the steps described need not occur in the order illustrated, but can occur in a different order, and/or with intervening steps.

Thus, field testing can be efficiently and accurately performed using the measurement 202 and associated system and methods described herein. Continuous correction for multiple sample readings in series can be automatically made. Correction of contamination of active sensor environmental interfaces with solids or interfering ions can be performed.

According to embodiments of the inventive concept, multiple solutions of known value (e.g., at least 2) can be obtained to define a calibration curve that the sample media can then be plotted against. Samples typically have multiple components present in solution, and both the presence of these interferents as well as typical use-related drift can cause ion concentration sensors to slowly return values that are inaccurate or unrelated to the actual concentration in the sample system. Embodiments of the inventive concept can correct for interferent-related drift in a single re-measurement.

Embodiment of the inventive concept can use the difference between the device reading of the reference pre-sample from the same reference post-sample to determine the inherent deviation from nominal operation. This can then be applied in a scalar fashion to the sample reading to correct the output. The pre-sample reading can either be directly one of the calibration solutions, or can be extrapolated from the nominal value that would have been read in a working calibration. Embodiments of the inventive concept provide for the measurement to be made in the linear portion of the device response regime.

The following discussion is intended to provide a brief, general description of a suitable machine or machines in which certain aspects of the invention can be implemented. Typically, the machine or machines include a system bus to which is attached processors, memory, e.g., random access memory (RAM), read-only memory (ROM), or other state preserving medium, storage devices, a video interface, and input/output interface ports. The machine or machines can be controlled, at least in part, by input from conventional input devices, such as keyboards, mice, etc., as well as by directives received from another machine, interaction with a virtual reality (VR) environment, biometric feedback, or other input signal. As used herein, the term "machine" is intended to broadly encompass a single machine, a virtual machine, or a system of communicatively coupled machines, virtual machines, or devices operating together. Exemplary machines include computing devices such as personal computers, workstations, servers, portable computers, handheld devices, telephones, tablets, etc., as well as transportation devices, such as private or public transportation, e.g., automobiles, trains, cabs, etc.

The machine or machines can include embedded controllers, such as programmable or non-programmable logic devices or arrays, Application Specific Integrated Circuits (ASICs), embedded computers, smart cards, and the like. The machine or machines can utilize one or more connections to one or more remote machines, such as through a network interface, modem, or other communicative coupling. Machines can be interconnected by way of a physical and/or logical network, such as an intranet, the Internet, local area networks, wide area networks, etc. One skilled in the art will appreciate that network communication can utilize various wired and/or wireless short range or long range carriers and protocols, including radio frequency (RF), satellite, microwave, Institute of Electrical and Electronics Engineers (IEEE) 545.11, Bluetooth®, optical, infrared, cable, laser, etc.

Embodiments of the invention can be described by reference to or in conjunction with associated data including functions, procedures, data structures, application programs, etc. which when accessed by a machine results in the machine performing tasks or defining abstract data types or low-level hardware contexts. Associated data can be stored in, for example, the volatile and/or non-volatile memory, e.g., RAM, ROM, etc., or in other storage devices and their associated storage media, including hard-drives, floppy-disks, optical storage, tapes, flash memory, memory sticks, digital video disks, biological storage, etc. Associated data can be delivered over transmission environments, including the physical and/or logical network, in the form of packets, serial data, parallel data, propagated signals, etc., and can be used in a compressed or encrypted format. Associated data can be used in a distributed environment, and stored locally and/or remotely for machine access.

Having described and illustrated the principles of the invention with reference to illustrated embodiments, it will be recognized that the illustrated embodiments can be modified in arrangement and detail without departing from such principles, and can be combined in any desired manner. And although the foregoing discussion has focused on particular embodiments, other configurations are contemplated. In particular, even though expressions such as "according to an embodiment of the invention" or the like are used herein, these phrases are meant to generally reference embodiment possibilities, and are not intended to limit the invention to particular embodiment configurations. As used herein, these terms can reference the same or different embodiments that are combinable into other embodiments.

Embodiments of the invention may include a non-transitory machine-readable medium comprising instructions executable by one or more processors, the instructions comprising instructions to perform the elements of the inventive concepts as described herein.

Consequently, in view of the wide variety of permutations to the embodiments described herein, this detailed description and accompanying material is intended to be illustrative only, and should not be taken as limiting the scope of the invention. What is claimed as the invention, therefore, is all such modifications as may come within the scope and spirit of the following claims and equivalents thereto.

The invention claimed is:
1. A portable ion concentration apparatus, comprising:
a controller;
a storage section coupled to the controller and configured to store one or more data samples and associated one or more timestamps received from the controller;

an amplifier circuit;
an ion concentration measurement device coupled to the amplifier circuit, wherein the ion concentration measurement device and the amplifier circuit are configured to indicate a quantity of ion levels of an ion in at least one of a sample media or a reference media,
wherein the controller is configured to process the indication of the quantity of ion levels, and generate the one or more data samples based at least on the indication of the quantity of ion levels; and
a measurement logic section configured to determine an ion concentration of the ion of the sample media based at least on a first electromotive force value, a second electromotive force value, and a polynomial fit.

2. The portable ion concentration apparatus of claim 1, further comprising a sensor module configured to receive ion concentration information of an ion from the amplifier circuit, and to provide the ion concentration information of the ion to the controller,
wherein the controller is configured to process the ion concentration information of the ion, and generate the one or more data samples based at least on the ion concentration information.

3. The portable ion concentration apparatus of claim 2, further comprising:
a reference section configured to store one or more known ion concentrations of ions corresponding to one or more reference media;
a temperature measurement section including a temperature sensor coupled to the amplifier circuit, and configured to sense a temperature of at least one of the sample media or the reference media; and
a communications section coupled to the controller, and configured to wirelessly transmit the one or more data samples.

4. The portable ion concentration apparatus of claim 3, wherein the portable ion concentration apparatus is a portable in-field analysis apparatus, comprising:
a display configured to visibly present the ion concentration information of the ion associated with at least one of the sample media or the reference media; and
a probe coupled to the portable in-field analysis apparatus via a cable, wherein the probe includes the ion concentration measurement device.

5. The portable ion concentration apparatus of claim 4, wherein the probe is configured to be sequentially inserted into the sample media and the reference media, and the controller is configured to correct for at least one of inherent nitrate, contamination of the sample media, or sample-to-sample drift.

6. The portable ion concentration apparatus of claim 5, wherein the sample media includes soil and water.

7. The portable ion concentration apparatus of claim 3, wherein the portable ion concentration apparatus is a portable in-field measurement apparatus, comprising:
one or more prongs disposed toward a bottom of the apparatus;
one or more moisture sensors attached to the one or more prongs for insertion into soil; and
one or more light emitting diodes (LEDs) configured to indicate status information.

8. The portable ion concentration apparatus of claim 7, wherein the one or more prongs are configured to be inserted directly into the soil without a need for preparing separate sample media, and sequentially inserted into the reference media, and wherein the controller is configured to correct for at least one of inherent nitrate or sample-to-sample drift.

9. A portable ion concentration apparatus comprising:
a controller;
a storage section coupled to the controller and configured to store one or more data samples and associated one or more timestamps received from the controller;
an amplifier circuit;
an ion concentration measurement device coupled to the amplifier circuit, wherein the ion concentration measurement device and the amplifier circuit are configured to indicate a quantity of ion levels of an ion in at least one of a sample media or a reference media,
wherein the controller is configured to process the indication of the quantity of ion levels, and generate the one or more data samples based at least on the indication of the quantity of ion levels; and
a measurement logic section configured to determine an ion concentration of an ion of the sample media based at least on a first electromotive force value, a second electromotive force value, and a sensitivity slope M.

10. The portable ion concentration apparatus of claim 9, wherein:
the measurement logic section is configured to determine the ion concentration of the ion of the sample media according to a formula:

$$\text{Value} = \text{Ion} * 10^{\left[\frac{[Read-(Ref-(Slope*Log(\frac{Known}{Ion})))]}{Slope}\right]};$$

Value refers to the ion concentration of the sample media;
Ion refers to a weight of ion to be measured multiplied by one thousand (1000);
Read refers to the first electromotive force, wherein the first electromotive force is obtained during measurement of the sample media;
Ref refers to the second electromotive force, wherein the second electromotive force is obtained during measurement of the reference media;
Slope refers to the sensitivity slope M; and
Known refers to an ion concentration of the reference media in parts per million.

11. The portable ion concentration apparatus of claim 1, wherein the measurement logic section is configured to determine the ion concentration of the ion of the sample media according to a first formula:

$$\text{Value} = \text{Ion} * 10^{\left[\frac{-B^2+\sqrt{B^2-4A((C-Shift)-Read)}}{2A}\right]};$$

the measurement logic section is configured to determine the ion concentration of the of the ion sample media according to a second formula:

$$\text{Shift} = \left(\left(A*\left(\log\left(\frac{Known}{Ion}\right)\right)^2\right) + B*\log\left(\frac{Known}{Ion}\right) + C\right) - Ref;$$

Value refers to the ion concentration of the ion of the sample media;
Ion refers to a weight of the ion to be measured multiplied by one thousand (1000);
Read refers to the first electromotive force, wherein the first electromotive force is obtained during measurement of the sample media;

Ref refers to the second electromotive force, wherein the second electromotive force is obtained during measurement of the reference media;

A refers to an A Coefficient in a polynomial equation form of $Y=Ax^2+Bx+C$;

B refers to a B Coefficient in the polynomial equation form of $Y=Ax^2+Bx+C$;

C refers to a C Coefficient in the polynomial equation form of $Y=Ax^2+Bx+C$; and Known refers to an ion concentration of the reference media in parts per million.

12. An in-soil monitoring apparatus, comprising:

a controller;

a storage section coupled to the controller and configured to store one or more data samples and associated one or more timestamps received from the controller;

an amplifier circuit;

an ion concentration measurement device coupled to the amplifier circuit, wherein the ion concentration measurement device and the amplifier circuit are configured to indicate a quantity of ion levels of an ion in at least one of a sample media or a reference media;

an outer housing configured to at least partially contain the controller, the storage section, the amplifier circuit, and the ion concentration measurement device in a semi-permanent location within soil, wherein the controller is configured to process the indication of the quantity of ion levels, and generate the one or more data samples based at least on the indication of the quantity of nitrato ion levels;

a sensor module configured to receive ion concentration information of an ion from the amplifier circuit, and to provide the ion concentration information of the ion to the controller, wherein the controller is configured to process the ion concentration information of the ion, and generate the one or more data samples based at least on the ion concentration information of the ion;

a reference section configured to store one or more known ion concentrations of ions corresponding to one or more reference media;

a temperature measurement section including a temperature sensor coupled to the amplifier circuit, and configured to sense a temperature of at least one of the sample media or the reference media;

a first near-field communication chip coupled to the controller, and configured to transmit the one or more data samples over a short-range communication link; and a second near-field communication chip in a host probe device located above a ground level within the outer housing, and configured to receive the one or more data samples from the first near-field communication chip.

13. The in-soil monitoring apparatus of claim 12, further comprising a long-range communications section in the host probe device located above the ground level within the outer housing, and configured to wirelessly transmit the one or more data samples over a long-range communication link.

* * * * *